United States Patent
Freeman

Patent Number: 5,968,001
Date of Patent: Oct. 19, 1999

[54] WOUND DRESSINGS WITH LEAK PREVENTION SEAL

[75] Inventor: Frank Freeman, Bahamas, United Kingdom

[73] Assignee: Bristol-Myers Squibb Company, New York, N.Y.

[21] Appl. No.: 08/796,094

[22] Filed: Feb. 5, 1997

Related U.S. Application Data

[60] Provisional application No. 60/017,563, May 14, 1996.

[51] Int. Cl.[6] ........................................ A61F 13/00
[52] U.S. Cl. .................................. 602/42; 602/48; 602/52
[58] Field of Search ................. 602/41–59, 79; 604/382, 384, 365–367, 370, 388.1

[56] References Cited

U.S. PATENT DOCUMENTS

| | | | |
|---|---|---|---|
| 4,390,519 | 6/1983 | Sawyer | 424/28 |
| 4,443,512 | 4/1984 | Delvaux | 428/162 |
| 4,578,071 | 3/1986 | Buell | 604/379 |
| 4,678,464 | 7/1987 | Holtman | 604/385 R |
| 4,738,257 | 4/1988 | Meyer et al. | 128/156 |
| 4,743,499 | 5/1988 | Volke | 428/317.3 |
| 4,762,124 | 8/1988 | Kerch et al. | 128/156 |
| 4,867,748 | 9/1989 | Samuelsen | 604/336 |
| 4,936,839 | 6/1990 | Molee et al. | 604/378 |
| 4,977,892 | 12/1990 | Ewall | 128/156 |
| 5,185,009 | 2/1993 | Sitnam | 604/364 |
| 5,267,992 | 12/1993 | Van Tilburg | 604/387 |
| 5,350,370 | 9/1994 | Jackson et al. | 604/367 |
| 5,447,505 | 9/1995 | Valentine et al. | 604/304 |
| 5,645,849 | 7/1997 | Pruss et al. | 424/426 |

*Primary Examiner*—Richard J. Apley
*Assistant Examiner*—Kim M. Lee
*Attorney, Agent, or Firm*—John M. Kilcoyne; Theodore R. Furman, Jr.

[57] ABSTRACT

A wound dressing having a lower skin-contacting layer, an upper occlusive layer and an absorbent layer therebetween, at least one seal is provided which defines an absorbent region for preventing the migration of body fluids from the absorbent region and to provide a moist wound environment including the optional inclusion of a wound healing substance.

25 Claims, 1 Drawing Sheet

WOUND DRESSINGS WITH LEAK PREVENTION SEAL

This application claims benefit of Provisional application Ser. No. 60/017,563, filed May 14, 1996.

FIELD OF THE INVENTION

The present invention is directed to wound dressings having a designated absorbent region defined by a substantially liquid impervious seal which enables the uptake and storage of body fluids while maintaining a moist environment about the wound.

BACKGROUND OF THE INVENTION

Wound dressings with layers for absorbing body fluids are known in the art. Absorbent layers are provided for the uptake of body fluids, especially wound exudate so as to enable the wound to be maintained by the wound dressing in a wound-healing environment.

Much effort has been directed to enhancing the rate of uptake and the capacity of the wound dressing, particular the absorbent layer, to uptake body fluids. In response to this quest, absorbent layers in wound dressings have been provided with hydrocolloids, superabsorbents, and synthetic materials which have extensive capacity to absorb body fluids, especially wound exudate such as disclosed in Assignee's pending U.S. application Ser. No. 08/519,433 filed Aug. 25, 1995, incorporated herein by reference.

Increasing the capacity and rate of fluid uptake within a wound dressing creates problems, particularly in assuring that body fluids do not migrate from the wound dressing. The migration of body fluids, particularly wound exudate from the wound dressing, is disadvantageous because the migrating fluid a) can contaminate the area adjoining the wound area, b) is aesthetically unpleasant for the patient and c) can contaminate medical personnel which is especially a problem in the treatment of patients with communicable diseases such as AIDS and hepatitis, and d) dry the wound bed.

It would therefore be a significant advance in the wound dressing art to form wound dressings which have the advantages of highly absorbent layers for the uptake of body fluids as well as the ability to retain the body fluids within a designated and limited absorbent region so that body fluids do not escape beyond the boundary of the wound dressing. It would be a further advance in the art if the wound dressing could provide a moist environment about the wound for rapid healing of the wound either through moisture from the body fluids or through the addition of moisture alone or in combination with a wound healing substance.

SUMMARY OF THE INVENTION

The present invention is generally directed to wound dressings capable of uptaking body fluids including wound exudate in which an absorbent region is separated from the remainder of the wound dressing by a sealing system that insures that body fluids can not readily migrate from the wound dressing. The absorbent region, formed by the sealing of a designated area of the wound dressing, enables the rapid uptake of body fluids while maintaining a moist environment about the wound. Moisture is provided from body fluids and/or added fluids which may optionally contain a wound healing substance.

More specifically, the present invention is directed to a wound dressing comprising:

a) a substrate comprising a lower skin-contacting layer, an upper occlusive layer and an absorbent layer therebetween for the uptake of a body fluid; and b) at least one seal circumscribing at least a portion of substrate to form an absorbent region sufficient to at least substantially prevent said body fluid from migrating out of the absorbent region, said wound dressing being capable of providing a moist environment about a wound which the wound dressing covers.

In a preferred form of the invention, the wound dressing is provided with liquid and/or solid wound healing substances which also can provide moisture to the wound. The liquid and/or solid wound healing substances may be provided during the making of the wound dressing or added just before the wound dressing is applied to the patient or during the healing process itself.

In addition, the designated absorbent region may comprise less than the entire surface area of the wound dressing. Outside of the designated absorbent region and separated therefrom by the at least one seal is a region stretching to the boundary of the wound dressing which may, optionally possess body fluid absorbing capacity.

Furthermore, wound healing substances may be provided to the wound dressing by incorporating the same into the absorbent region. Such substances can be in the form of solutions, suspensions, creams, lotions, ointments, gels and the like.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

The present invention is generally directed to a wound dressing comprised of an upper occlusive layer, a lower skin-contacting layer and an absorbent layer therebetween for the uptake of body fluids such as wound exudate. An absorbent region is enclosed within and defined by one or more seals placed within the perimeter of the wound dressing. The seal prevents migration of the body fluid from the absorbent region while retaining a moist environment about the wound.

Figure 1:
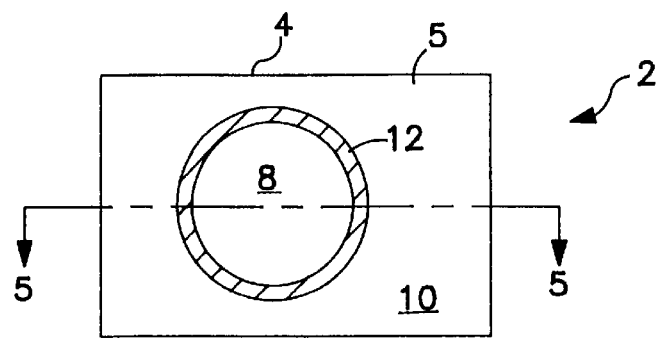
FIG. 1 is a plan view of one embodiment of the wound dressing of the present invention.
Figure 2:
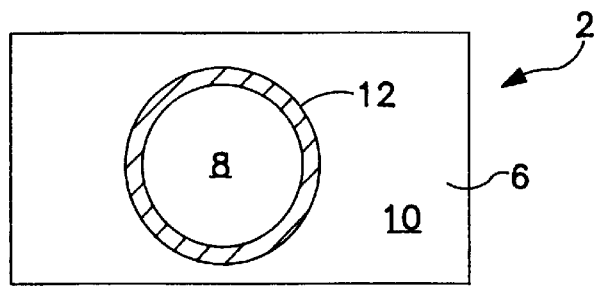
FIG. 2 is a bottom view of the embodiment of the wound dressing shown in FIG. 1.

Referring to FIGS. 1 and 2 there is shown an embodiment of the invention employing a single seal to define a designated absorbent region which is placed directly over the wound. The wound dressing 2 of the present invention includes a substrate 4 having an upper occlusive layer 5 and a lower skin-contacting layer 6. An absorbent layer as more fully described hereinafter (see FIGS. 5 and 6) is positioned between the occlusive layer 5 and the skin-contacting layer 6. The absorbent layer is capable of uptaking body fluids and storing the same away from the wound area. An absorbent region 8 comprising portions of the occlusive layer 5, the skin-contacting layer 6 and the absorbent layer is separated from the remaining portion 10 of the wound dressing by at least one seal 12 as described in detail hereinafter. The seal 12 is sufficient to at least substantially prevent body fluids, such as wound exudate from migrating from the absorbent region 8 outside of the boundaries of the wound dressing 2. The seal 12 in conjunction with the occlusive layer 5 forms a moisture barrier that is particularly adapted for maintaining the wound in a moist environment.

As shown in FIGS. 1 and 2, the wound dressing 2 and particularly the absorbent region 8 is circumscribed by a single, circular seal 12. The seal can be formed by applying energy to the wound dressing or by the application of a substance which alone or through the application of energy can form a desirable seal. It is preferred therefore that the materials used to form the layers of the wound dressing as described herein be capable of forming a seal when energy is applied thereto. Thermoplastic materials are particularly useful for this purpose.

In a preferred form of the invention, the seal is formed by the application of energy which provides a water impervious barrier by sealing together portions of the occlusive layer 5, the absorbent layer and the skin-contacting layer 6 to form the absorbent region 8. The preferred seals are formed from ultrasonic energy or thermal energy. When using ultrasonic energy or thermal energy, it is essential that the materials forming the wound dressing be sealable by the type of energy which is employed as explain ed hereinafter.

Alternatively, the seal can be formed from a substance which is impervious to the passage of body fluids. Examples of such materials include adhesives, caulking compounds, water impervious polymers such as ethylene vinyl acetate compounds. The seals can be formed from such materials by applying the same to the wound dressing during manufacture and allowing the material to set. In another method water-impervious materials are coated onto the fibers or other components of the wound dressing and then energy is applied (e.g. thermal or ultrasonic energy) or the fibers are compressed to form the seal.

Figure 3:
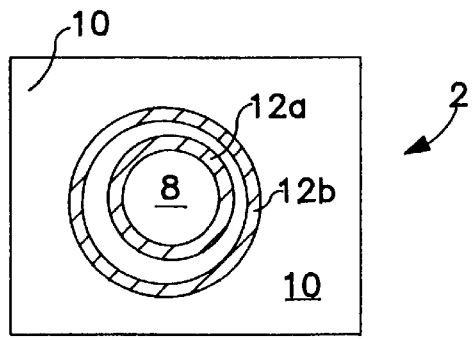
FIG. 3 is a plan view of another embodiment of a wound dressing in accordance with the present invention.

The wound dressing 2 of the present invention can comprise a plurality of seals to form the absorbent region 8. Referring to FIG. 3, there is shown an embodiment of the wound dressing 2 in which two seals 12a and 12b are employed to separate the absorbent region 8 from the remaining portion 10 of the wound dressing 2. The seals 12a and 12b may be formed by any of the same methods described above and may each be formed of the same or different methods. For example, the inner seal 12a may be formed by the application of ultrasonic or thermal energy and the outer seal 12b may be formed of a different method such as by the use of a water-impervious sealing material (e.g. an adhesive).

Multiple seals can be used when the amount of body fluid expected to be absorbed is excessive. The outer seal(s) (e.g. seal 12b as shown in FIG. 3) provides additional protection against migration of the body fluid from the absorbent region 8.

Figure 4:
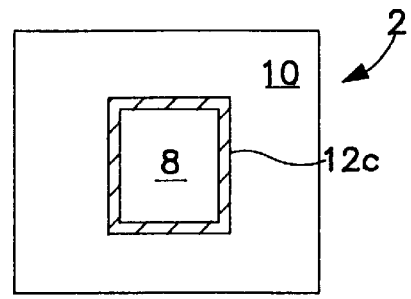
FIG. 4 is a plan view of a still further embodiment of a wound dressing in accordance with the present invention.

The shape of the seal is unlimited so long as the seal circumscribes an adsorbent region which covers the wound. Thus, the shape of the seal can be circular, rectangular, in the form of a square, a polygon or can be irregular shaped such as in the form of a decorative design (e.g. cartoon character) and the like. By way of example, reference is made to FIG. 4 showing a rectangular shaped seal 12c.

The composition of the wound dressing can vary so long as there is an upper occlusive layer, a skin-contacting layer and an absorbent layer therebetween circumscribed by at least one seal in accordance with the present invention to form an absorbent region. The wound dressing can therefore include a variety of absorbent materials and skin-contacting materials.

It is an essential feature of the present invention that the wound dressing be capable of absorbing body fluids in a designated absorbent region while maintaining the wound area in a moist environment. Thus, the absorbent region must comprise the combination of materials which will promote fluid absorption and wound healing. The amount of the body fluid absorbing materials within the absorbent region 8 can vary according to the amount of body fluids which must be absorbed.

Figure 5:
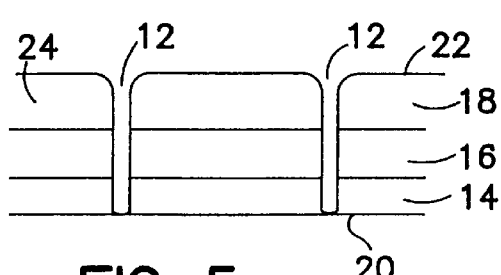
FIG. 5 is a partial cross-sectional view of a preferred embodiment of the wound dressing which has a single circular seal defining the absorbent region.
Figure 6:
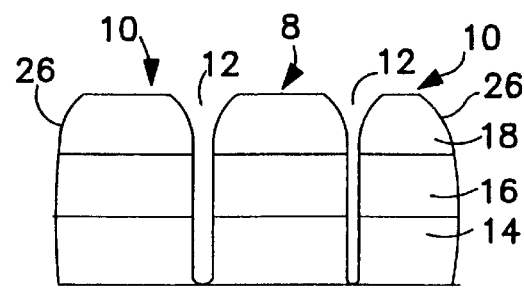
FIG. 6 is a partial cross-sectional view of an embodiment of the invention similar to FIG. 5 with a second seal around the periphery of the wound dressing.

A preferred composition of the wound dressing of the present invention is shown in FIGS. 5 and 6. Referring first to FIG. 5, the wound dressing 2 includes a skin-contacting layer 14, an absorbent layer 16 and an occlusive layer 18. A seal 12 is provided to form an absorbent region 8 which uptakes and stores body fluids.

The skin-contacting layer 14 is the layer that remains in contact with the skin during application of the wound dressing. In accordance with the present invention, the skin-contacting layer serves to protect the wound dressing while allowing moisture to pass therethrough. In addition, the skin-contacting layer is adherent (i.e. having a material thereon such as an adhesive which adheres the wound dressing to the skin).

Permeability of the skin-contacting layer 14 to moisture is made possible by mechanical means such as by providing slits or perforations in the skin-contacting layer. Alternatively, permeability can be provided through the use of hydrocolloids or similar fluid transporting materials which, by absorbing and then desorbing fluid creates discontinuities within the skin-contacting layer.

The skin-contacting layer is typically made from polymeric materials, preferably thermoplastics which can be thermally or ultrasonically sealed. The preferred polymeric materials for the skin-contacting layer are polyolefins especially isobutylene based polymers. One preferred construction is a lower layer of an adhesive formed from a combination of high and low molecular weight polyisobutylene, mineral oil and tackifiers. Alternatively, an acrylic based adhesive containing hydrocolloids can be used. The hydrocolloids pickup and transport moisture through the skin-contacting layer. An upper layer of the skin-contacting layer is preferably made of a polyolefin composition such as polyethylene, copolymers of polyolefins including vinyl acetate, and the like. The skin contact layer can be made in the form of a perforated, laminated or coextruded film to impact the desired moisture transition properties.

The combination of the upper and lower components of the skin-contacting layer allows moisture to enter the absorbent layer of the absorbent region while maintaining the area about the wound in a moist environment.

The skin-contacting layer 14 has a skin contacting surface 20 with optionally a skin-compatible adhesive thereon. When an adhesive is not used, the wound dressing may be taped or wrapped in place. The adhesive can be applied to the entire skin contacting surface 20 or only a portion thereof such as that portion which does not overlie the wound.

An adhesive is preferably placed on the bottom surface of the skin-contacting layer. The adhesive composition may be any suitable adhesive such as one based on a high molecular weight polyisobutylene or an acrylic based adhesive. The adhesive may include a homogeneous blend of one or more pressure sensitive adhesive materials and one or more natural or synthetic polymers capable of developing elastomeric properties when hydrated such as gluten and long chain polymers of methyl vinyl ether/maleic acid. The composition may also include one or more water-soluble hydrocolloid gums and may additionally include one or more water swellable cohesive strengthening agents. Additionally, one or more thermoplastic elastomers may be included with the pressure sensitive adhesive materials.

Various natural or synthetic viscous or elastomeric substances as natural rubber, silicone rubber, acrylonitrile rubber, polyurethane rubber, polyisobutylene, and the like, either possessing dry tack by themselves or developing such tack upon the addition of a plasticizer are suitable as adhesives. Low molecular weight polyisobutylenes having a viscosity average molecular weight of from about 36,000 to about 58,000 (Florey) may also be used.

The adhesive coating can suitably have a thickness of 0.5 mil to 1.5 mil. The adhesive coating can be a continuous or a discontinuous coating, for example, a pattern, porous or microporous coating.

The absorbent layer 16 for use in wound dressings of the present invention can be constructed of absorbent materials useful in medical settings and typically is in the form of a web, net, foam, perforated film, or the like having hydrocolloids and/or superabsorbents dispersed therein.

In a preferred form of the invention, the absorbent layer is comprised of a thermoplastic material such as polyolefin, or a polyester. The preferred polyolefin is polypropylene. In a preferred form of the invention, the absorbent layer 16 comprises a matrix of polypropylene with hydrocolloids and/or superabsorbents dispersed therein. The purpose of the hydrocolloids and superabsorbents is to trap fluid within the polymeric matrix.

As shown specifically in FIGS. 5 and 6, the wound dressing 2 has an occlusive layer 18. The occlusive layer 18 has an upper or outer surface 22 which is open to the atmosphere and an inner surface 24 which faces the absorbent layer 16. The occlusive layer 18 is comprised of materials that are generally impervious to fluid transmission. The occlusive layer 18 preferably has a moisture vapor transmission rate (MVTR) in the range of about 100 to 800 $g/m^2$, most preferably from about 400 to 800 $g/m^2$ although the upper limit for some applications can be as high as 4000 $g/m^2$ or greater, as may be required. The latter MVTR is in instances where larger dressings are needed and treatment requires that a portion of the wound fluid be evaporated through the dressing.

The occlusive layer 18 may be made of any soft film having a MVTR within the above range. Some preferred materials include polyurethanes, polyolefins such as linear low density polyethylene, low density polyethylene and ethylene vinyl acetate, Sarans materials such as vinylidene chloride copolymers of vinyl chloride, methyl acrylate, or methyl methacrylate copolymers. A preferred polymeric material is polyurethane, either as a film or as a polyurethane foam. The polyurethane could be an ester or ether based polyurethane having a 6800 psi and an elongation of from 300 to 750. The water vapor transmission rate (WVTR) of such polyurethane is preferably from 100 to 4000 $g/m^2$ (ASTM). One preferred polyurethane film is Medifilm.

Other materials which can be used in the occlusive layer are styrene copolymers such as styrene-butadiene-styrene (S-B-S), styrene-isoprene-styrene (S-I-S) and styrene-ethylene/butylene-styrene (S-EB-S), methyl methacrylate copolymers, polyethylene copolymers and nitrile rubber.

Another material that may be used as the occlusive layer is a foam or fiber combination where there is a layer of foam or fiber which has a film layer adhered thereto. The foam used in these dressings is generally a polyethylene or polyurethane foam laminated to about 0.5 mil polyester film. The foam preferably has a density of about 0.042–0.057 gm/sq. in.

The skin-contacting layer 14 may be bonded to the occlusive layer 18 and the absorbent region 16 with suitable adhesives such as acrylic or suitable hot melts. Instead of such adhesives the skin-contacting layer may be bonded to the film by heat or ultrasonic bonding or thermoplastic adhesives.

A release paper (not shown) is typically applied to wound dressings to cover the surface of the wound dressing which is to contact the skin. Release papers for wound dressings are well known.

The hydrocolloid materials useful for the skin-contacting layer and the absorbent layer include any water soluble gum (e.g. pectin, guar gum, xantham gum), gelatin, carboxymethylcellulose (CMC), such as sodium CMC, sodium or calcium alginates, polysaccharides and the like.

The superabsorbent materials useful for the absorbent layer may be in any suitable form. Typical superabsorbents include starch grafted copolymers of acrylate salts, starch grafted copolymers of acrylamide salts, polyacrylate salts and the like, including mixtures thereof. Superabsorbent materials and composites are easily prepared or commercially available. The superabsorbent web can also be formed by needle punching processes. The superabsorbent may also be a delayed release web superabsorbent.

As previously indicated, the wound dressing may be provided with a liquid or solid substance to provide moisture to the wound and/or to provide a wound healing substance thereto. The liquid or solid substance is administered through the skin-contacting layer into the absorbent layer either during manufacture of the wound dressing or prior to applying the wound dressing to the patient.

The preferred substance for providing moisture to the wound area is saline. For the application of a wound healing substance to the wound dressing the liquid or solid substance can be in the form of a solution, suspension, cream, ointment, gel, powders, particulates, including but not limited to lyophilized materials and the like. The active ingredients which can be added to the wound dressing in such forms include antiseptics, antibiotics such as tetracycline, erythromycin, gentamicin and the like, and saline and the like.

In alternate embodiment of the present invention as shown in FIG. 6, the occlusive layer 18 and the adjacent lower layers can be compressed and then sealed to form a tapered edge.

More specifically, the dressing 2 has an edge portion 26 which is sealed as described before into a thin edge portion having a thickness of preferably from about 2 to 5 mils. The embodiment represented by FIG. 6 is prepared by taking the embodiment of FIGS. 1 and 2 and sealing the edge portion 26.

What is claimed is:
1. A wound dressing comprising:
  a) a substrate comprising a lower skin-contacting layer, an upper occlusive layer and an absorbent layer therebetween for the uptake of a body fluid;

b) at least one seal circumscribing at least a portion of the substrate to form an absorbent region sufficient to at least substantially prevent said body fluid from migrating out of the absorbent region; and c) means for maintaining a moist environment about a wound which the wound dressing covers comprising a moist environment maintaining substance.

2. The wound dressing of claim 1 comprising a plurality of seals.

3. The wound dressing of claim 2 comprising a plurality of concentric seals.

4. The wound dressing of claim 1 wherein the seal is formed from an adhesive.

5. The wound dressing of claim 1 wherein the seal is formed by the selective application of energy to the substrate.

6. The wound dressing of claim 5 wherein the seal is formed by treating the substrate with thermal or ultrasonic energy.

7. The wound dressing of claim 1 wherein said skin-contacting layer, said absorbent layer and said occlusive comprise heat sealable or ultrasonic sealable materials.

8. The wound dressing of claim 1 wherein the moist environment maintaining substance is saline.

9. The wound dressing of claim 1 wherein the moist environment maintaining substance is at least one wound healing substance.

10. The wound dressing of claim 9 wherein the wound healing substance is in a form selected from the group consisting of a solution, suspension, cream, ointment, gel, powder, particulate material and mixtures thereof.

11. The wound dressing of claim 9 wherein the wound healing substance is selected from the group consisting of antiseptics, antibiotics and saline.

12. The wound dressing of claim 1 wherein the skin-contacting layer allows the passage of moisture therethrough.

13. The wound dressing of claim 12 wherein the skin-contacting layer comprises a polyolefin.

14. The wound dressing of claim 13 wherein the skin-contacting layer comprises two layers, a lower layer comprising an adhesive and an upper layer comprising a material selected from the group consisting of a polyolefin and copolymers of polyolefins.

15. The wound dressing of claim 12 wherein the skin-contacting layer further comprises a material for promoting the passage of moisture therethrough.

16. The wound dressing of claim 15 wherein the material is a hydrocolloid.

17. The wound dressing of claim 1 wherein the skin-contacting has an adhesive thereon for adhering the wound dressing to the skin.

18. The wound dressing of claim 1 wherein the skin-contacting layer is selected from the group consisting of a perforated film, a laminated film, and a coextruded film.

19. The wound dressing of claim 1 wherein the absorbent layer is in the form of a web, net, foam or perforated film.

20. The wound dressing of claim 1 wherein the absorbent layer contains hydrocolloids, superabsorbents or a combination thereof.

21. The wound dressing of claim 20 wherein the absorbent layer comprises a matrix of a polyolefin having said hydrocolloids, superabsorbents or a combination thereof dispersed therein.

22. The wound dressing of claim 21 wherein the absorbent layer comprises a matrix of polypropylene.

23. The wound dressing of claim 1 wherein the occlusive layer has a moisture vapor transmission rate of up to about 4000 g/m$^2$.

24. The wound dressing of claim 23 wherein the moisture vapor transmission rate is from about 100 to 800 g/m$^2$.

25. The wound dressing of claim 24 wherein the moisture vapor transmission rate is from about 400 to 800 g/m$^2$.

* * * * *